United States Patent
Milijasevic et al.

(10) Patent No.: US 9,642,982 B2
(45) Date of Patent: May 9, 2017

(54) MODULAR CATHETER ASSEMBLY

(75) Inventors: Zoran Milijasevic, Bayview (AU);
Jesse Woolaston, Cremorne (AU);
David Ogle, Cowan (AU)

(73) Assignee: CathRx LTD., Homebush Bay, NSW (AU)

( * ) Notice: Subject to any disclaimer, the term of this patent is extended or adjusted under 35 U.S.C. 154(b) by 1242 days.

(21) Appl. No.: 12/299,117

(22) PCT Filed: May 4, 2007

(86) PCT No.: PCT/AU2007/000601
§ 371 (c)(1),
(2), (4) Date: Aug. 3, 2009

(87) PCT Pub. No.: WO2007/128065
PCT Pub. Date: Nov. 15, 2007

(65) Prior Publication Data
US 2010/0036392 A1    Feb. 11, 2010

Related U.S. Application Data

(60) Provisional application No. 60/798,254, filed on May 5, 2006, provisional application No. 60/835,501, filed on Aug. 4, 2006.

(51) Int. Cl.
*A61B 17/00* (2006.01)
*A61M 25/00* (2006.01)
(Continued)

(52) U.S. Cl.
CPC .... *A61M 25/0043* (2013.01); *A61M 25/0133* (2013.01); *A61M 25/0136* (2013.01);
(Continued)

(58) Field of Classification Search
CPC .............................. A61N 1/05–1/0597; A61N 2001/0578–2001/0585;
(Continued)

(56) References Cited

U.S. PATENT DOCUMENTS 3,847,140 A * 11/1974 Ayella .......................... 600/585
4,940,064 A *  7/1990 Desai ........................... 607/122
(Continued)

FOREIGN PATENT DOCUMENTS

EP    0962191    12/1991
EP    0898940    3/1999
(Continued)

OTHER PUBLICATIONS

International Search Report mailed on Jul. 11, 2007, for PCT Application No. PCT/AU2007/000601, filed on May 4, 2007, eight pages.

(Continued)

*Primary Examiner* — Victor Nguyen
*Assistant Examiner* — Jonathan Hollm
(74) *Attorney, Agent, or Firm* — TraskBritt

(57) ABSTRACT

A modular catheter assembly includes a holder, having a proximal end and a distal end. An electrode sheath carrier is mounted on the distal end of the holder. A shape-imparting element carrier is removably mountable to an end of the holder and is accessible externally of the holder with at least the shape-imparting element carrier being replaceably mounted to the holder.

25 Claims, 5 Drawing Sheets

(51) Int. Cl.
*A61M 25/01* (2006.01)
*A61N 1/05* (2006.01)
*A61B 18/14* (2006.01)
*A61M 39/10* (2006.01)

(52) U.S. Cl.
CPC .......... *A61N 1/056* (2013.01); *A61B 18/1492* (2013.01); *A61B 2017/003* (2013.01); *A61M 39/10* (2013.01)

(58) Field of Classification Search
CPC .................... A61M 25/0133–25/0152; A61M 2025/015–2025/0163
USPC ...... 606/108, 129; 600/585; 604/95.01, 528; 607/41
See application file for complete search history.

(56) References Cited

U.S. PATENT DOCUMENTS

| | | | |
|---|---|---|---|
| 5,117,839 A * | 6/1992 | Dance | 600/585 |
| 5,170,787 A * | 12/1992 | Lindegren | 600/373 |
| 5,190,050 A * | 3/1993 | Nitzsche | 600/585 |
| 5,327,905 A * | 7/1994 | Avitall | 600/585 |
| 5,441,504 A | 8/1995 | Pohndorf et al. | |
| 5,487,757 A | 1/1996 | Truckai et al. | |
| 5,607,392 A * | 3/1997 | Kanner | 604/86 |
| 5,617,854 A | 4/1997 | Munsif | |
| 5,634,881 A | 6/1997 | Francis | |
| 5,656,029 A * | 8/1997 | Imran et al. | 604/95.04 |
| 5,656,030 A * | 8/1997 | Hunjan et al. | 604/95.01 |
| 5,662,119 A * | 9/1997 | Brennen et al. | 600/585 |
| 5,674,271 A | 10/1997 | Denker | |
| 5,722,403 A | 3/1998 | McGee et al. | |
| 5,882,333 A * | 3/1999 | Schaer et al. | 604/95.01 |
| 5,941,817 A | 8/1999 | Crawford | |
| 5,987,344 A * | 11/1999 | West | 600/373 |
| 5,997,526 A | 12/1999 | Giba et al. | |
| 6,059,739 A * | 5/2000 | Baumann | 600/585 |
| 6,102,926 A * | 8/2000 | Tartaglia et al. | 606/170 |
| 6,126,657 A | 10/2000 | Edwards et al. | |
| 6,217,574 B1 | 4/2001 | Webster | |
| 6,221,070 B1 | 4/2001 | Tu et al. | |
| 6,251,092 B1 * | 6/2001 | Qin et al. | 604/95.01 |
| 6,332,880 B1 | 12/2001 | Yang et al. | |
| 6,611,710 B2 * | 8/2003 | Gomperz et al. | 607/7 |
| 7,551,968 B2 | 6/2009 | Flach et al. | |
| 7,947,000 B2 | 5/2011 | Vargas et al. | |
| 2003/0014037 A1 | 1/2003 | Thompson et al. | |
| 2003/0130620 A1 | 7/2003 | Alokaili | |
| 2003/0135230 A1 | 7/2003 | Massey et al. | |
| 2003/0139794 A1 | 7/2003 | Jenney et al. | |
| 2003/0181855 A1 | 9/2003 | Simpson et al. | |
| 2003/0216711 A1 * | 11/2003 | Rabiner et al. | 604/528 |
| 2004/0127915 A1 * | 7/2004 | Fleenor et al. | 606/144 |
| 2005/0060885 A1 | 3/2005 | Johnson et al. | |
| 2005/0085883 A1 | 4/2005 | Ollivier et al. | |
| 2005/0182387 A1 | 8/2005 | Webler | |
| 2006/0142694 A1 | 6/2006 | Bednarek et al. | |
| 2006/0168805 A1 | 8/2006 | Hegland et al. | |
| 2008/0045921 A1 * | 2/2008 | Anderson et al. | 604/508 |

FOREIGN PATENT DOCUMENTS

| | | |
|---|---|---|
| EP | 0980693 | 2/2000 |
| EP | 0982047 | 3/2000 |
| EP | 1400208 A1 | 3/2005 |
| EP | 1512427 A2 | 9/2005 |
| EP | 1 618 917 A2 | 1/2006 |
| WO | WO-98/02201 A1 | 1/1998 |
| WO | WO-99/56810 A1 | 11/1999 |
| WO | WO-01/37723 A2 | 5/2001 |
| WO | WO-01/37723 A3 | 5/2001 |
| WO | WO-02/32497 A1 | 4/2002 |
| WO | 2004039273 A2 | 5/2004 |
| WO | WO-2004/100813 A2 | 11/2004 |
| WO | WO-2004/100813 A3 | 11/2004 |
| WO | WO-2005/051216 A1 | 6/2005 |
| WO | WO-2005/070491 A2 | 8/2005 |
| WO | WO-2005/070491 A3 | 8/2005 |
| WO | WO-2005/094661 A1 | 10/2005 |
| WO | 2006012671 A1 | 2/2006 |
| WO | WO-2006/012668 A1 | 2/2006 |
| WO | WO-2006/092016 A1 | 9/2006 |
| WO | WO-2006/092016 C1 | 9/2006 |
| WO | WO-2006/135988 A1 | 12/2006 |

OTHER PUBLICATIONS

Written Opinion mailed on Jul. 11, 2007 for PCT Application No. PCT/AU2007/000601, filed on May 4, 2007, six pages.
U.S. Appl. No. 60/798,254, filed May 5, 2006, for Milijasevic et al.
U.S. Appl. No. 60/835,501, filed Aug. 4, 2006, for Milijasevic et al.
Australian Examination Report for AU Application No. 2007247769, dated Mar. 11, 2011, 4 pages.
Japanese Search Report for JP Application No. P2009-508052, dated May 24, 2011, 7 pages.
Supplemental European Search Report for EP Application No. 07718848.0, dated Jun. 10, 2010, 9 pages.
International Preliminary Report on Patentability for PCT Application No. PCT/AU2007/000601, mailed Nov. 11, 2008.
Supplemental European Search Opinion for EP Application No. 07718848.0, 1 page.
Supplemental European Search Report for EP Application No. 07718848.0, 1 page.
European Search Report dated Aug. 21, 2013, for EP Application No. 13166897, filed May 5, 2006, 11 pages.

* cited by examiner

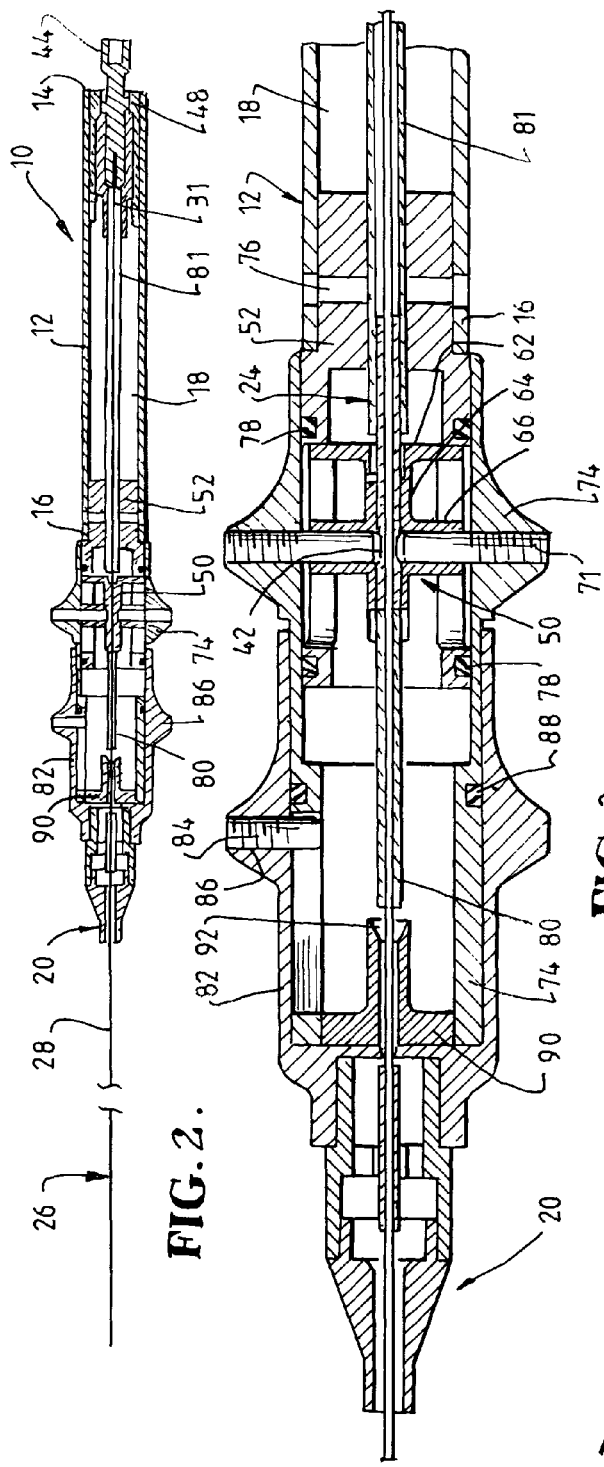
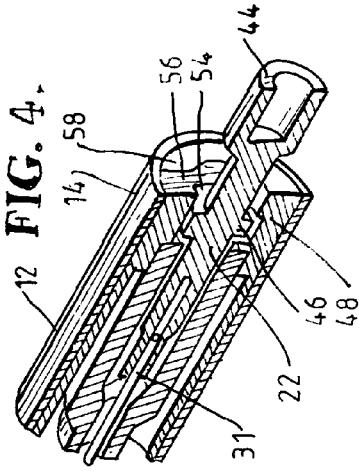
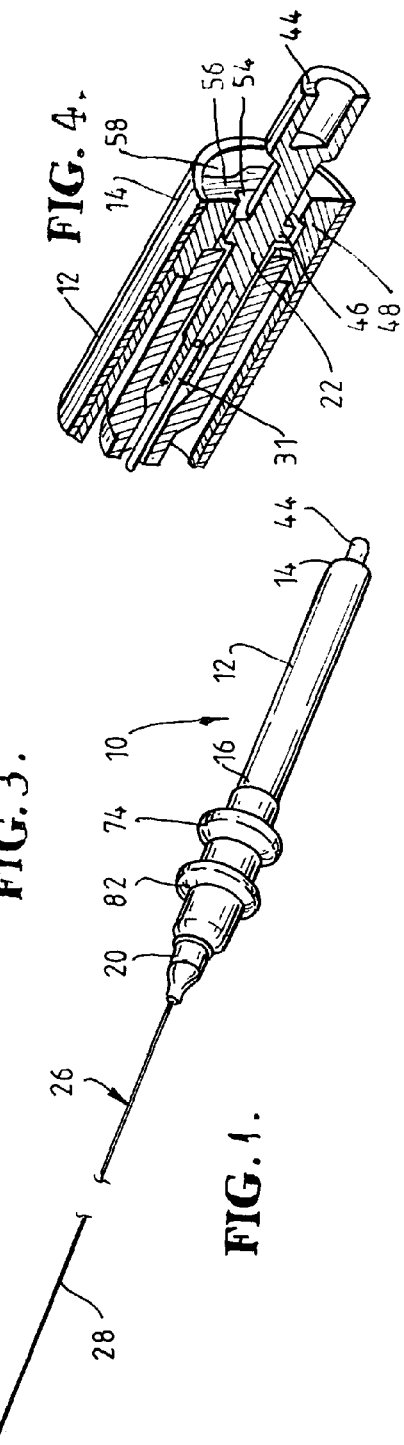

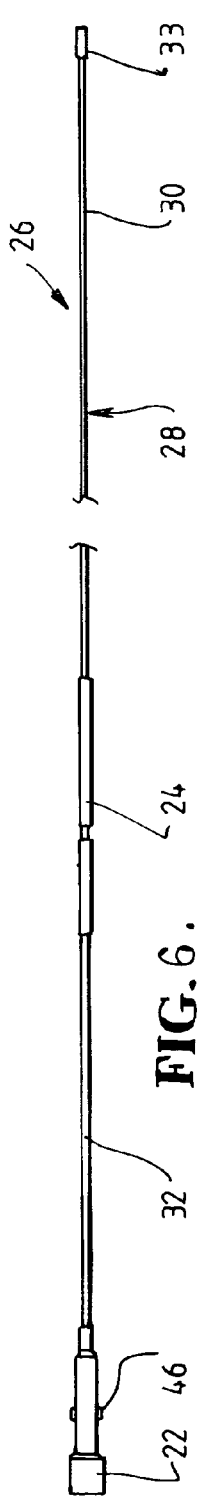
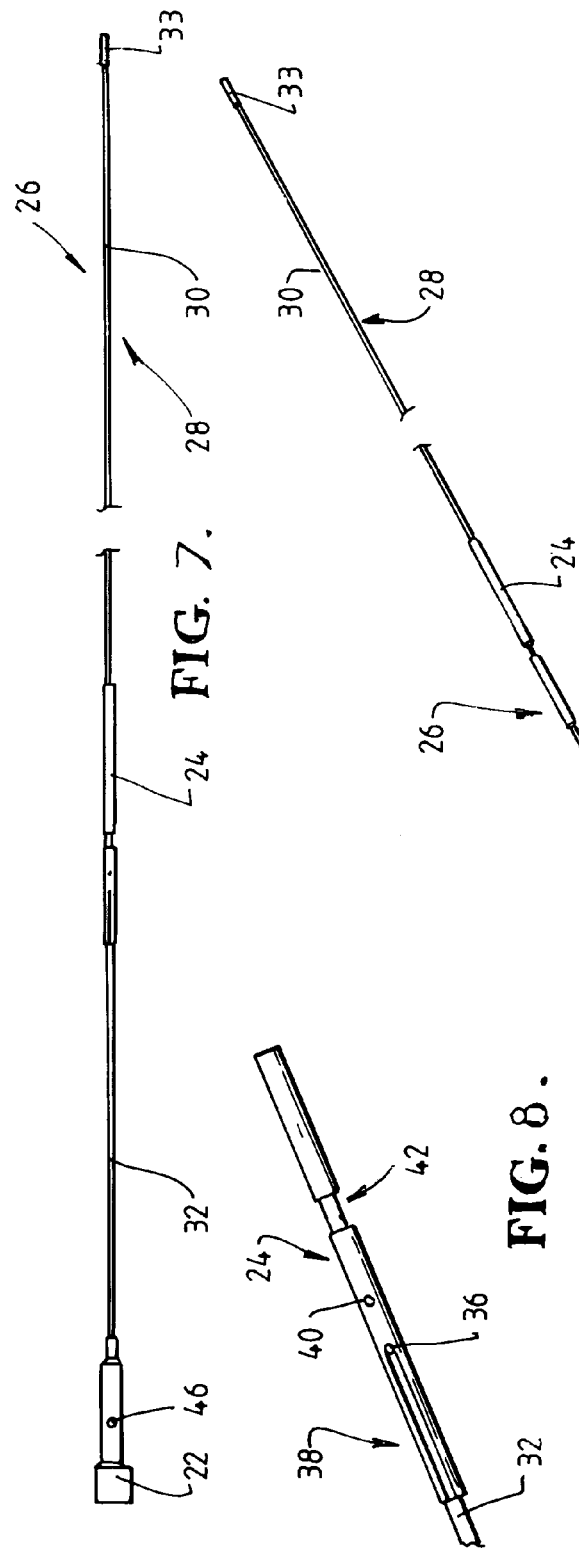
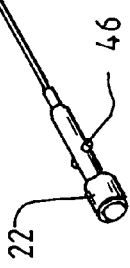

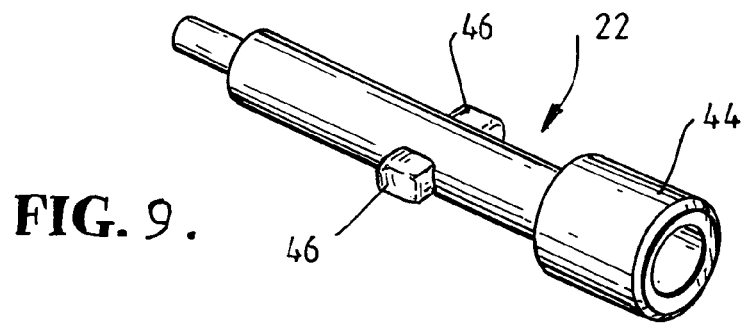
FIG. 9.
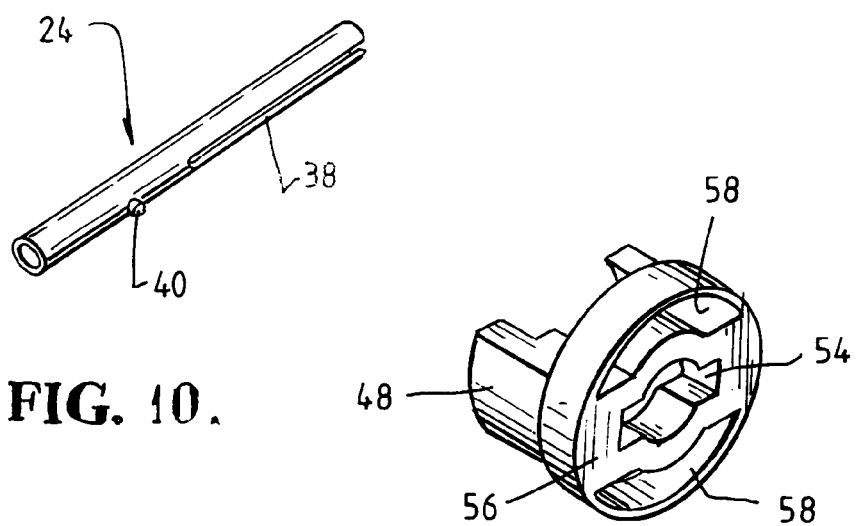
FIG. 10.
FIG. 11.
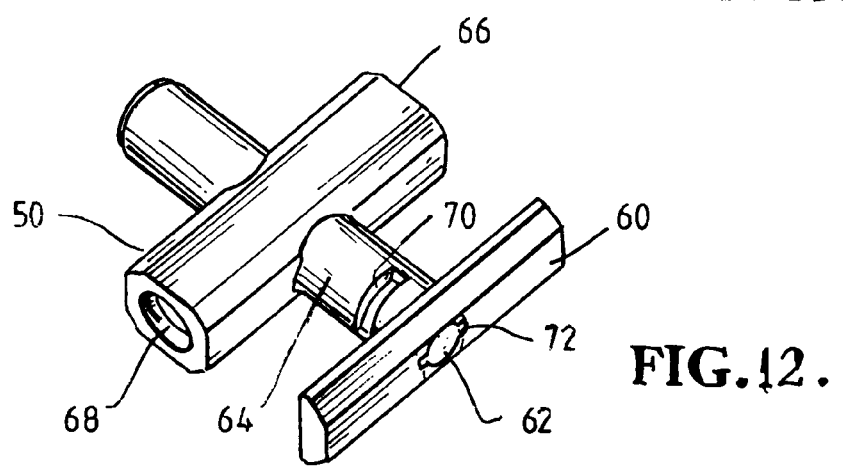
FIG. 12.

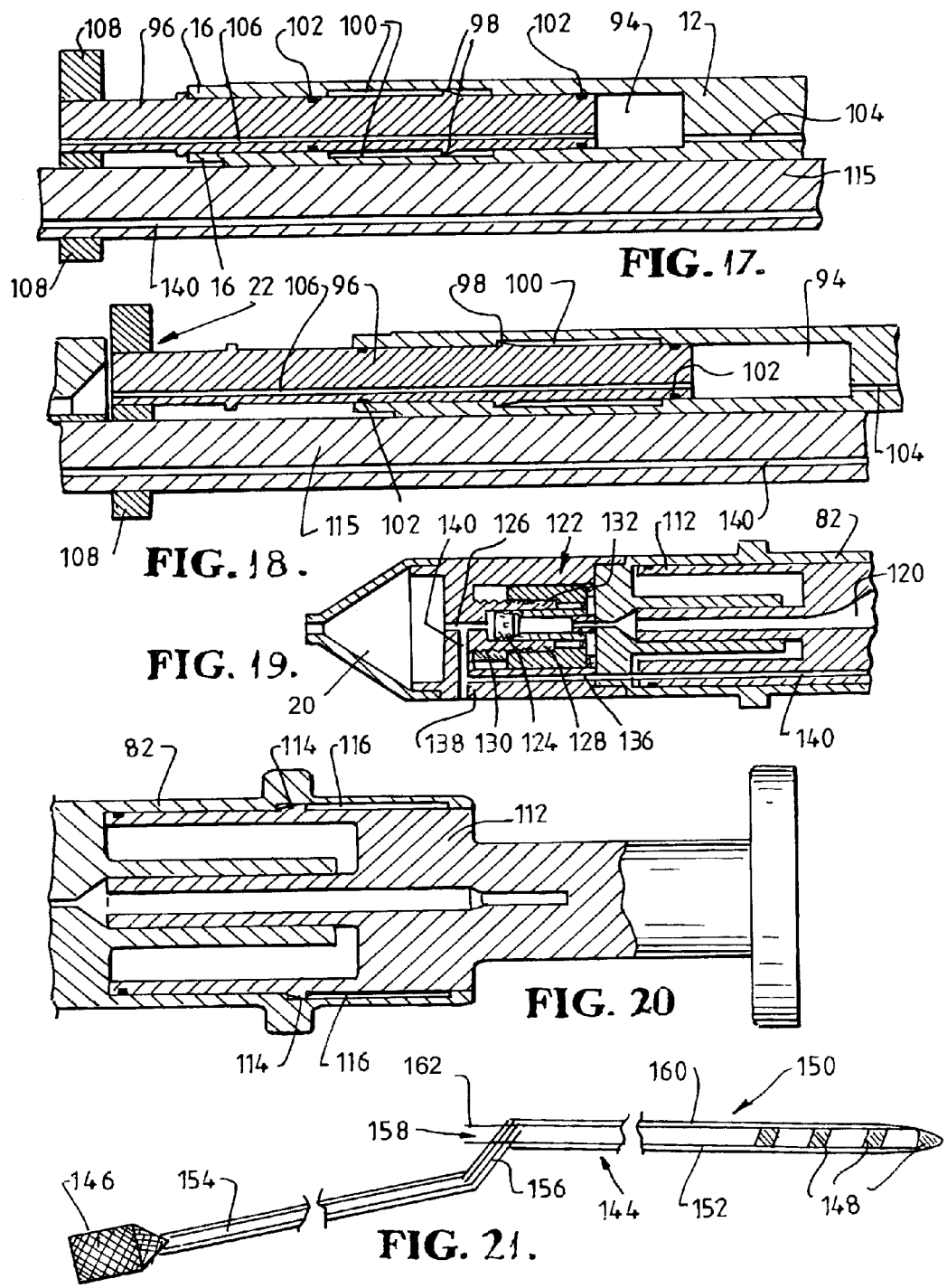

MODULAR CATHETER ASSEMBLY

CROSS-REFERENCE TO RELATED APPLICATIONS

This application is a National Phase entry under 35 U.S.C. §371 of International Application No. PCT/AU2007/000601, filed May 4, 2007, which claims the benefit of U.S. Provisional Patent Application No. 60/798,254, filed May 5, 2006, and U.S. Provisional Patent Application No. 60/835,501, filed Aug. 4, 2006, the contents of which are incorporated herein by reference in their entirety.

FIELD

This invention relates, generally, to catheters and, more particularly, to a modular catheter assembly and to components for a modular catheter assembly.

BACKGROUND

Catheters, such as those used in cardiovascular applications, are comprised of an elongate electrode-carrying element mounted on a distal end of a handle. The handle has at least one connector so that a patient cable can be connected to a proximal end of the handle to feed signals through the handle to the electrodes. Often, these catheters include steering mechanisms or stylets arranged within the electrode-carrying element to effect steering and/or deflection of a distal end of the electrode-carrying element.

Such an arrangement results in an expensive piece of equipment, particularly, the handle, which has the at least one connector and cabling. Also, because of voids in the electrode-carrying element and in the interior of the handle, it is not possible, generally, to effect sufficient sterilization of such catheters enabling them to be reused. Thus, in most cases, the catheters are used once only and are then disposed of.

Not only does this create a substantial expense, but there is the environmental problem of disposal of potentially hazardous items.

SUMMARY

According to a first aspect of the invention, there is provided a modular catheter assembly that includes:
- a holder having a proximal end and a distal end;
- an electrode sheath carrier mounted on the distal end of the holder; and
- a shape-imparting element carrier removably mountable to an end of the holder and being accessible externally of the holder with at least the shape-imparting element carrier being replaceably mounted to the holder.

In this specification, the term "shape-imparting element" is to be understood in a broad sense to include any device which imparts a shape to the electrode sheath of the catheter whether adjustably, such as a steering shaft (with or without a fixed curve portion), or non-adjustably, such as a fixed curve stylet.

The shape-imparting element carrier may be replaceable to be sterilized and reused and/or to be replaced by a different shape-imparting element carrier carrying a different shape-imparting element.

The holder may comprise an elongate element defining an axially extending bore.

The shape-imparting element carrier may comprise a boss having a proximal end and a distal end. The assembly may include a shape-imparting element carried on the shape-imparting element carrier, the shape-imparting element comprising an elongate tubular member with an actuator received in the elongate tubular member, at least one of the actuator and the tubular member being mounted to the distal end of the boss.

The boss may be received within the bore of the holder. The shape-imparting element carrier may comprise a connector arranged distally of the boss and connected to the boss, one of the tubular member and the actuator of the shape-imparting element being fast with the connector and the other of the tubular member and the actuator being fast with the boss.

In one embodiment, the bore of the holder may be an open passageway extending from the proximal end of the holder to the distal end of the holder, the holder defining receiving formations and the boss and the connector comprising corresponding engaging formations that engage their associated receiving formations in the bore of the holder for retaining the shape-imparting element in position relative to the holder.

A first receiving formation may be arranged at the proximal end of the holder and a second receiving formation may be arranged distally of the first receiving formation, the second receiving formation being displaceably arranged within the bore of the holder. The second receiving formation may be fast with a control mechanism, the control mechanism being axially displaceably arranged on the holder and being accessible externally of the holder.

The electrode sheath carrier may be mounted on a displacement mechanism, the displacement mechanism being arranged on the distal end of the holder. The displacement mechanism may be displaceably arranged relative to the control mechanism on the holder.

Both the first receiving formation and the second receiving formation may be shaped to permit the passage of at least one electrical conductor past the first receiving formation and the second receiving formation. The catheter may be an irrigation catheter and the receiving formations may also be shaped to allow an irrigation conduit received in the bore of the housing to pass through the receiving formations.

In another embodiment, the bore of the holder may be a blind bore defined at the distal end of holder. Once again, in this embodiment, the assembly may include a shape-imparting element carried on the shape-imparting element carrier, the shape-imparting element comprising an elongate tubular member with an actuator received in the elongate tubular member. The shape-imparting element carrier may be removably received within the blind bore, one of the tubular members and the actuator of the shape-imparting element being fast with the shape-imparting element carrier and the other of the tubular member and the shape-imparting element being fast with the holder.

The shape-imparting element carrier may function as a control mechanism for controlling the shape of the shape-imparting element carried on the shape-imparting element carrier, the control mechanism being axially displaceable relative to the holder.

The electrode sheath carrier may be arranged distally of the shape-imparting element carrier, the electrode sheath carrier having a proximally extending mount received in a distal part of the holder.

The electrode sheath carrier may include a displacement mechanism displaceably arranged, axially, on the mount for effecting axial displacement of the electrode sheath relative to the shape-imparting element, in use.

In this embodiment, the assembly may include a first sealing element interposed between the shape-imparting element carrier and the distal end of the holder for inhibiting the ingress of material into the bore of the holder. The first sealing element may include a bellows-like member arranged over a proximal part of the shape-imparting element carrier. The assembly may further include a second sealing element arranged in the electrode sheath carrier between the mount and the displacement mechanism for inhibiting the ingress of material into the interior of the electrode sheath carrier.

According to a second aspect of the invention, there is provided a catheter shape-imparting element assembly that includes:

a shape-imparting element comprising an elongate tubular member with an actuator received within the tubular member, the actuator being fast with the tubular member at a distal region of the tubular member;

a first member to which one of the tubular member and the actuator is connected; and a second member, displaceably arranged relative to the first member to which the other of the tubular member and the actuator is connected.

In one embodiment, the first member may be a boss received within a catheter handle holder and the second member may be a connector receivable within the holder distally of the boss.

In another embodiment, the first member may be a handle of a catheter assembly and the second member may be a control mechanism displaceably arranged at a distal end of the holder.

According to a third aspect of the invention, there is provided an electrical lead that includes:

a lumen-defining member, the lumen-defining member having a discontinuity along its length to create a proximal part and a distal part;

a plurality of conductors carried on an outer surface of the lumen-defining member, the plurality of conductors being separated from the lumen-defining member at the discontinuity to enable access to be gained to a lumen defined by the distal part, the plurality of conductors electrically bridging the discontinuity;

a covering over the plurality of conductors, the covering being removed at the discontinuity to enable access to be gained to the plurality of conductors at the discontinuity; and at least one electrode carried on the covering at a distal part of the lumen-defining member.

The electrical lead may be used with the catheter assembly as described above, a proximal end of the distal part of the lumen-defining member being secured to a distal end of the electrode sheath carrier, the electrode sheath carrier defining a passage through which the proximal part of the lumen-defining member and the plurality of conductors pass to extend internally within the holder and to exit through the proximal end of the holder.

According to a fourth aspect of the invention, there is provided a catheter that includes:

a modular catheter assembly as described above;

an electrode sheath carried on a distal end of the electrode sheath carrier; and a shape-imparting element received within a lumen of the electrode sheath, the shape-imparting element passing through the electrode sheath carrier and being secured within the holder via the shape-imparting element carrier.

The electrode sheath may be the electrical lead as described above.

BRIEF DESCRIPTION OF DRAWINGS

FIG. 1 shows an isometric view of a modular catheter assembly, in accordance with a first embodiment of the invention;

FIG. 2 shows a sectional side view of the assembly of FIG. 1;

FIG. 3 shows, on an enlarged scale, a sectional side view of a portion of the assembly of FIG. 2;

FIG. 4 shows a three-dimensional view of a proximal part of the assembly;

FIG. 5 shows an isometric view of a shape-imparting element assembly in accordance with another embodiment of the invention;

FIG. 6 shows a side view of the shape-imparting element assembly of FIG. 5;

FIG. 7 shows a plan view of the shape-imparting element assembly;

FIG. 8 shows an isometric view of a part of the shape-imparting element assembly;

FIG. 9 shows an isometric view of a boss of the shape-imparting element assembly;

FIG. 10 shows an isometric view of a connector of the shape-imparting element assembly;

FIG. 11 shows an isometric view of a first receiving formation of the modular catheter assembly of FIGS. 1-4;

FIG. 12 shows an isometric view of a second receiving formation of the modular catheter assembly of FIGS. 1-4;

FIG. 17 shows a schematic, sectional side view of a part of the assembly of FIGS. 13 and 14, in a retracted position;

FIG. 18 shows a sectional side view of the part of the assembly of FIG. 17 in an extended position;

FIG. 19 shows a sectional side view of a distal part of the assembly of FIGS. 13 and 14 in a retracted position;

FIG. 20 shows a schematic, sectional side view of a portion of the part of the assembly of FIG. 19; and FIG. 21 shows a schematic representation of a modification to an electrode sheath for use with the assembly of FIGS. 13 and 14.

DETAILED DESCRIPTION OF THE INVENTION

Figure 13:
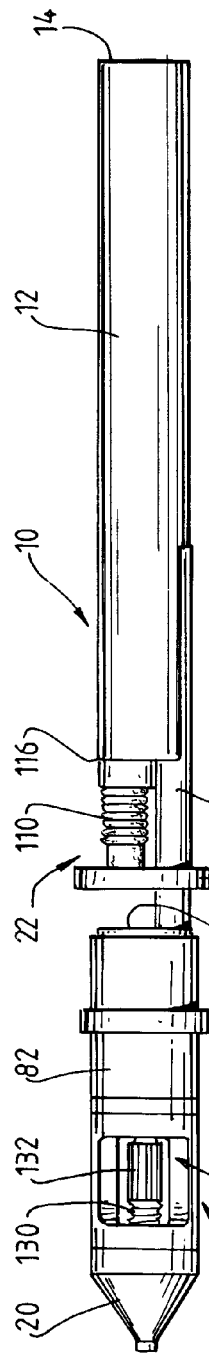
FIG. 13 shows a side view of a modular catheter assembly in accordance with a second embodiment of the invention, with a distal part in a retracted position.
Figure 14:
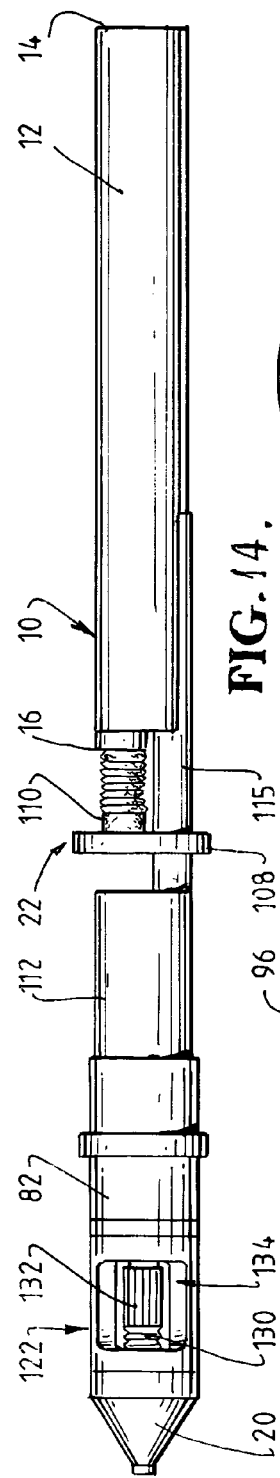
FIG. 14 shows a side view of the assembly of FIG. 13 with the distal part in an extended position.

In FIGS. 1-12 of the drawings, reference numeral 10 generally designates a modular catheter assembly, in accordance with a first embodiment of the invention. The assembly 10 comprises a holder 12 having a proximal end 14 and a distal end 16. The holder 12 defines an elongate, open passageway or bore 18 through it.

An electrode sheath carrier 20 is mounted to a distal end of the holder 12. A shape-imparting element carrier, comprising a boss 22 (shown more clearly in FIG. 9) and a connector 24 (shown more clearly in FIG. 10), is removably mountable within the bore 18 of the holder 12.

The boss 22 and the connector 24 form part of a shape-imparting element assembly 26 (FIGS. 5-7). The assembly 26 includes a shape-imparting element in the form of a steering shaft 28. The steering shaft 28 is of the type having an outer tubular element 30 and an inner actuator 31 (FIG. 4), which is shown in FIGS. 5-8 covered by a sleeve 32. The steering shaft 28 is of the type described in the Applicant's co-pending International Patent Application No. PCT/AU2005/000216 dated Feb. 18, 2005 and titled "A Steerable Catheter."

Thus, the actuator 31 is fast with the tubular member 30 at a distal end 33 of the steering shaft 28. It is to be noted that the actuator 31 projects from a proximal end of the tubular member 30. The connector 24 is, therefore, connected to the proximal end of the tubular member 30. The actuator 31 passes through the connector 24, a proximal part of the actuator 31 is covered by the sleeve 32 and the boss 22 is mounted at the proximal end of the actuator 31 of the steering shaft 28, as shown in FIG. 4.

The sleeve 32 is received within the proximal end of the connector 24. The sleeve 32 is retained in position by a radially outwardly extending pin 36 being received in an axially extending slot 38 in the connector 24.

The connector 24, itself, has an engaging formation in the form of a radially outwardly extending pin 40 arranged distally of the slot 38. A waisted region 42 is defined in the connector 24 distally of the pin 40.

The boss 22 has an enlarged, outer cylindrical formation 44, which can be gripped for manipulating the assembly 26. As illustrated in FIGS. 2 and 4, the enlarged cylindrical outer formation 44 projects outwardly from the proximal end 14 of the holder 12 to be externally accessible.

The boss 22 has an engaging formation in the form of a pair of opposed, radially outwardly extending protuberances or lugs 46, the purpose of which will be described in greater detail below.

The assembly 10 includes a first receiving formation or component 48 arranged at the proximal end 14 of the holder 12 and a second receiving formation or component 50 arranged in a slide support 52 at the distal end 16 of the holder 12. The component 48 has a keyway-shaped slot 54 defined in an outer face 56. The keyway-shaped slot 54 is shaped to allow passage of the lugs 46 of the boss 22 through it. The spacing between an operatively inner end of the enlarged formation 44 and the lugs 46 is such that, when the boss 22 is pushed home relative to the component 48, the lugs 46 are arranged distally of the keyway-shaped slot 54. A quarter-turn of the boss 22, therefore, locks the boss 22 relative to the formation 48.

It is to be noted, that openings 58 are arranged on opposed sides of the slot 54 in the face 56 of the formation 48. These openings 58 allow electrical connectors for an electrode sheath (not shown) to pass through the bore 18 of the holder 12 and out through the proximal end of the holder 12. The openings 58 also allow the passage of an irrigation tube when the catheter assembly 10 is used as an irrigation catheter.

The component 50 has a proximal opening defining a member 60 defining a keyed opening 62. The member 60 is mounted to the end of a sleeve 64. The sleeve 64 supports a socket-defining member 66 defining a pair of opposed, threaded sockets 68 in which grub screws 71 (FIG. 3) are receivable.

The sleeve 64 has an L-shaped slot 70 defined in it, an axially extending part of the slot 70 being in communication with a key 72 of the keyed opening 62. In use, the pin 40 of the connector 24 is received within the key 72 of the opening 62 and into the axially extending part of the L-shaped slot 70. When the assembly 26 is rotated through 90°, the pin 40 is received in a circumferentially extending part of the L-shaped slot 70, locking the shape-imparting element assembly 26 in position relative to the catheter assembly 10. Thus, the arrangement of the L-shaped slot 70 of the component 50 functions as a "bayonet-type" locking system to lock the assembly 26 in position relative to the assembly 10. Once again, it is to be noted that the component 50 has a substantially flattened shape to allow the passage of connectors and/or an irrigation tube past it.

As described above, the component 50 is slidably mounted in the slide support 52. The slide support 52 supports a slide 74. The slide 74 functions as a control mechanism for controlling bending of the distal end 33 of the steering shaft 28. The slide 74 is secured to the component 50 via the grub screws 71, the grub screws 71 engaging the waisted region 42 of the connector 24 to lock the slide 74 to the connector 24. The slide support 52 is fast with the distal end 16 of the holder 12 via grub screws (not shown) received in transversely extending bores 76 in the slide support 52.

The slide 74 sealingly engages the support 52 via a pair of sealing members, such as O-rings 78 arranged on opposed sides of the component 50.

To facilitate insertion of the steering shaft 28 through the holder 12 and the support 52, guide tubes 80, 81 are mounted to the component 50 and to the support 52, respectively.

A distal part of the slide 74 supports a displacement mechanism 82. The displacement mechanism 82 is axially displaceable relative to the slide 74 and, therefore, relative to the holder 12. The displacement mechanism 82 is also in the form of a slide and carries the electrode sheath carrier 20 on a distal part. The slide 82 is secured to the slide 74 via a grub screw 84. The grub screw 84 is received in an axially extending slot 86 in a distal part of the slide 74. The slot 86 limits the travel of the slide 82 relative to the slide 74.

Once again, to inhibit the ingress of material into the interior of the assembly 10, the slide 82 sealing engages the slide 74 via a sealing member, such as an O-ring 88.

A further guide element 90 is arranged at a distal region of the slide 82 for facilitating passage of the steering shaft 28. A proximal end of the guide element 90 has a funnel-shaped opening 92, which facilitates insertion of the distal end 33 of the steering shaft 28 into the guide element 90. It is to be noted that a distal end of the guide tube 80 terminates in close proximity to the opening 92 of the guide element 90, when the slide 82 is in a retracted position relative to the slide 74, to assist in inserting the steering shaft 28 into the opening 92.

In use, with this embodiment, a desired shape-imparting assembly 26, e.g., the steering shaft 28, is mounted to the holder 12 by inserting the boss 22 and the connector 24 into their associated components 48 and 50, respectively. The boss 22 and the connector 24 are locked to their associated components 48 and 50, respectively, by turning the boss 22 through 90°. An electrode sheath (not shown) of the assembly 10 can then be steered through the vasculature of a patient (not shown) to the desired site in the patient's body. If it is necessary to use another shape-imparting element 26, the one in use is removed and is replaced by such other shape-imparting element 26. This can be effected while the electrode sheath remains in situ.

Further, after use, the shape-imparting element 26, being the most expensive part of the assembly 10 can be removed for sterilization and re-use. The remainder of the assembly 10 can be disposed of.

Referring now to FIGS. 13-21 of the drawings, a second embodiment of a modular catheter assembly is illustrated. With reference to the previous drawings, like reference numerals refer to like parts, unless otherwise specified.

In this embodiment, the holder 12 defines a blind bore 94 (FIGS. 17 and 18) at the distal end 16. The boss 22 of the shape-imparting element carrier has a shaft 96, which is slidably received within the blind bore 94. The shaft 96 has retaining formations in the form of a pair of opposed clips 98. The clips 98 are received in channels 100 defined in the blind bore 94 that limit the degree of axial displacement of the shaft 96 relative to the holder 12. Seals, in the form of O-rings 102, are arranged on opposed sides of the clips 98 for sealing the blind bore 94 to inhibit the ingress of foreign material into the blind bore 94.

A tubular receiving formation 104 extends proximally into the holder 12 from a proximal end of the blind bore 94. The actuator of the shape-imparting element assembly 26 (not shown in this embodiment) is received in the tubular receiving formation 104 after passing through a passage 106 in the shaft 96 of the boss 22.

A distal end of the shaft 96 supports an engageable element 108 via which an operator can displace the boss 22 axially relative to the holder 12. The passage 106 opens out into a distal end of the engageable element 108. The tubular member 30 of the steering shaft 28 is attached to the distal end of the engageable element 108 about the opening of the passage 106 in a sealing manner.

To inhibit the ingress of material into the blind bore 94 of the holder 12, a seal, in the form of a bellows-like element 110, is arranged about the shaft 96 between the engageable element 108 and the distal end 16 of the holder 12.

The electrode sheath carrier 20 is mounted on a body member 112 (FIG. 19). The body member 112 slidably supports the displacement mechanism 82. As illustrated more clearly in FIG. 20, the displacement mechanism 82 clips to the body member 112 via a pair of opposed clips 114. The clips 114 are carried on the body member 112 and each clip 114 is received in an axially extending channel 116 defined in the displacement mechanism 82. In FIG. 13, the displacement mechanism 82 is shown in a retracted position on the body member 112. The displacement mechanism 82 is shown in an extended position relative to the body member 112 in FIG. 14.

An elongate mount 115 extends from a proximal end of the body member 112. The mount 115 is eccentrically arranged on the proximal end of the body member 112 and is received in a channel 117 (FIG. 15) of the holder 12. The channel 117 is arranged alongside, but not in communication with, the blind bore 94 at the distal region of the holder 12. It is to be noted that the channel 117 defines retaining formations 118 that retain the mount in position relative to the holder 12.

A proximal end of the body member 112 has a flared opening 120 to facilitate the insertion of the steering shaft 28 through the body member 112.

A sealing assembly 122 is, optionally, carried on the distal end of the body member 112. The sealing assembly 122 is used when the catheter with which the assembly 10 is used is an irrigation catheter. The sealing assembly 122 supports a sealing element 124 arranged about a passage 126 in the sealing assembly 122. The steering shaft 28 projects through the passage 126, in use. The sealing element 124 seals about the tubular member 30 of the steering shaft 28 and inhibits the ingress of foreign material and liquid into the body member 112. The sealing element 124 is a resiliently flexible element and is received in a Luer-type lock 128. The lock 128 carries an external screw thread 130 and a knurled wheel 132 is received on the threaded lock 128. The wheel 132 is accessible through a pair of opposed openings 134 in the sealing element 122. The sealing element 124 is urged into sealing abutment with the tubular member 30 of the steering shaft 28 by rotating the wheel 132 in a first direction. Conversely, to release the sealing element 124 from sealing abutment with the tubular member 30 of the steering shaft 28, the wheel 132 is rotated in the opposite direction. It will be appreciated that, if the catheter is not an irrigation catheter, the sealing assembly 122 can be omitted, with the electrode sheath carrier 20 being secured directly to the distal end of the body member 112.

As shown in greater detail in FIG. 19, the passage 126 communicates with an irrigation passage 136. The irrigation passage 136 follows a tortuous path through a wall 138 of the sealing assembly 122. The passage 136 continues as a further passage 140 in the body member 112.

Figure 16:
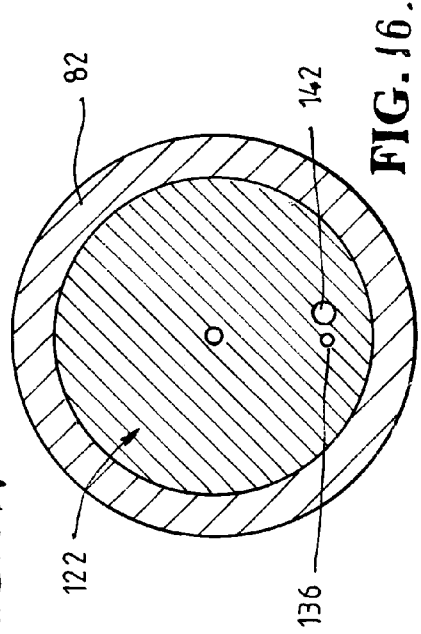
FIG. 16 shows a section end view of a further part of the assembly of FIGS. 13 and 14.
Figure 15:
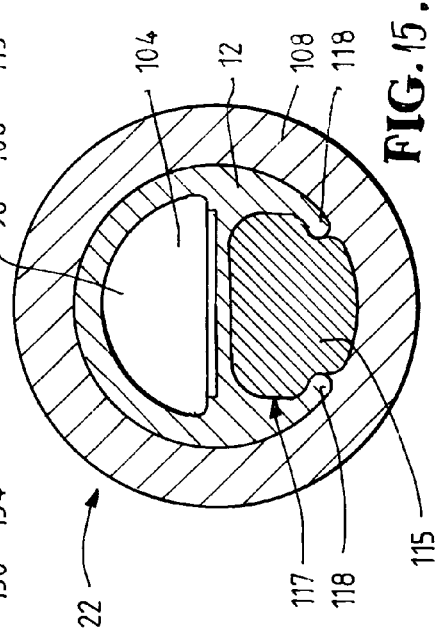
FIG. 15 shows a sectional end view of part of the assembly of FIGS. 13 and 14.

As shown more clearly in FIG. 16, the passage 136 is arranged alongside another passage 142. Electrical conductors from an electrode sheath 144 (FIG. 21) are received through the passage 142. Thus, an irrigation tube (not shown) received through the passage 136 and the electrical conductors extending through the passage 142 pass through the proximal end of the body member 112 and beneath the holder 12, in use. In particular, the electrical conductors of the electrode sheath 144 are connected to a connector 146 (FIG. 21) arranged proximally of the proximal end of the holder 12.

In FIG. 21, an electrical lead 150 defining the electrode sheath 144 is shown. The electrical lead 150 has a connector 146 at its proximal end and electrodes 148 at its distal end. The electrical lead 150 is substantially greater in length than the length of electrode sheath 144 required for use as a catheter. The electrical lead 150 has a distal part 152 that is of the requisite length to form the electrode sheath 144 of the catheter and a proximal part 154. The proximal part 154 and the distal part 152 are electrically connected to each other via conductors 156 of the electrical lead 150. However, the proximal part 154 and the distal part 152 are mechanically separated from each other via a discontinuity 158, the discontinuity 158 being electrically bridged by the conductors 156.

The discontinuity 158 is formed by removing an outer covering 160 from the electrical lead 150 in the region where the discontinuity 158 is to be formed. The conductors 154 are unwound from a lumen-defining portion 162 of the electrical lead 150. The electrical lead 150 is cut at a region to form the discontinuity 158 and the proximal part 154 and the distal part 152 of the electrical lead 150. A proximal end of the lumen-defining portion 162 of the distal part 152, which functions as the electrode sheath 144, is secured to a distal end of the electrode sheath carrier 20. The conductors 156 are threaded through the opening 142 and the proximal part 154 of the electrical lead 150 passes through the proximal end of the body member 112 and beneath the holder 12 to be connected via the connector 146 to a patient cable or other equipment (not shown).

In this embodiment of the invention, the holder 12, together with the shape-imparting element assembly 26 secured thereto, is reusable. The part of the assembly 10 arranged distally of the engageable element 108 is disposable. Thus, after use, the mount 115 is removed from the channel 117 and is disposed of. A new distal part of the assembly 10 is then attached to the holder 12 for subsequent use. Alternatively, while in use, the holder 12 with the shape-imparting element assembly 26 attached thereto can be removed from the distal part and replaced with another holder 12 carrying a different shape-imparting element assembly 26. For example, initially, a modular catheter assembly 10 using a steering shaft 28 may be used to steer a distal end of the catheter to the desired site in a patient's body (not shown). At the desired site, it may be desired to use a fixed curved stylet. While the catheter is in situ, the holder 12 with the steering shaft 20 secured thereto may be detached from the body member 112 by removing the mount 115 from the channel 117. A different holder 12 carrying a fixed curved stylet at its distal end may then be mounted on the mount 115 with the fixed curved stylet being threaded into the electrode sheath which is still in situ.

It is, therefore, an advantage of the invention that a modular catheter assembly 10 is provided that makes use of a reusable part, being at least the shape-imparting assembly 26. Parts of the assembly 10 that come into contact with bodily fluids can be disposed. In this regard, it is to be noted that the holder 12, having no electrical connectors therein, is a low-cost item. In addition, in the case of the first embodiment, because the holder 12 does not have any electrically conductive materials therein, it is easier to dispose of, for example, to a recycling plant. In the case of the second embodiment, a similar consideration applies in respect of the body member 112 and its associated parts. In other words, there are no electrically conductive elements in the part 112 and, thus, the part 112 and its associated parts can be disposed of in an environmentally friendly manner.

In addition, the ease with which the boss 22 can be detached from the holder 12 or the distal part 112, as the case may be, improves the versatility of the assembly allowing replacement shape-imparting elements to be used, as desired and with ease.

Further, when the handle of the catheter has an electrical connector at its distal end, it is necessary to insert the shape-imparting element through the connector. The connector has a very small opening, typically of a diameter in the order of 1-2 mm, centrally arranged in the connector. The opening is surrounded by electrical connections of the connector and it is difficult for a clinician to insert the shape-imparting element into the opening of the connector. With the absence of such a connector, a much larger opening, which may be funnel-shaped, may be provided at the distal end of the holder, which makes it much easier to insert the shape-imparting element through the distal end of the handle into the catheter sheath.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

The invention claimed is:

1. A modular catheter assembly, including:
   a holder having an axially extending bore, a proximal end and a distal end, wherein the holder includes a control mechanism being axially displaceably arranged on the holder and being accessible externally of the holder, wherein the control mechanism comprises a first receiving formation, wherein the holder comprises a second receiving formation at the proximal end of the holder, the first receiving formation comprising a first locking mechanism and the second receiving formation comprising a second locking mechanism;
   an electrode sheath carrier mounted on the distal end of the holder;
   a shape-imparting element carrier including a first engaging formation and a second engaging formation, wherein the first engaging formation and the first receiving formation and the second engaging formation and the second receiving formation are cooperatively configured for de-attachment and re-attachment of the shape-imparting element carrier with the control mechanism by operation of the first and second locking mechanisms, the first and second locking mechanisms operable by joint rotation of the first engaging formation and the second engaging formation of the shape-imparting element carrier relative to the holder, the shape-imparting element carrier configured to be unlocked from the holder by joint rotation of the first engaging formation and the second engaging formation of the shape-imparting element carrier relative to the holder; and
   a shape-imparting element carried on the shape-imparting element carrier, the shape-imparting element comprising an elongate tubular member extending outwardly from the distal end of the holder when the shape-imparting element carrier is attached with the holder, wherein the elongate tubular member is coupled to the shape-imparting element carrier and configured for removal from the holder with the shape-imparting element carrier when the shape-imparting element carrier and the control mechanism are de-attached, the elongate tubular member and the shape-imparting element carrier remaining coupled while the shape-imparting element carrier is de-attached from the control mechanism.

2. The modular catheter assembly of claim 1, wherein the shape-imparting element carrier comprises a connector comprising the first engaging formation.

3. The modular catheter assembly of claim 2, wherein the shape-imparting element further comprises an actuator received in the elongate tubular member, at least one of the actuator and the elongate tubular member being mounted to a distal end of the boss.

4. The modular catheter assembly of claim 3, wherein the boss is received within an axially-extending bore of the holder.

5. The modular catheter assembly of claim 3, wherein the shape-imparting element carrier comprises a boss arranged proximally of a connector and connected to the connector, wherein at least one of the elongate tubular member and the actuator of the shape-imparting element is fast with the connector and the other of the elongate tubular member and the actuator is fast with the boss.

6. The modular catheter assembly of claim 5, wherein an axially-extending bore of the holder is an open passageway extending from the proximal end of the holder to the distal end of the holder, and wherein the boss comprises the second engaging formation.

7. The modular catheter assembly of claim 1, wherein the second receiving formation is fast with a control mechanism, the control mechanism being axially displaceably arranged on the holder and being accessible externally of the holder.

8. The modular catheter assembly of claim 7, wherein the electrode sheath carrier is mounted on a displacement mechanism, the displacement mechanism being arranged on the distal end of the holder.

9. The modular catheter assembly of claim 8, wherein the displacement mechanism is displaceably arranged relative to the control mechanism on the holder.

10. The modular catheter assembly of claim 1, wherein both the first receiving formation and the second receiving formation are shaped to permit the passage of at least electrical conductors past the first receiving formation and the second receiving formation.

11. The modular catheter assembly of claim 10, wherein the electrical conductors extend past the first receiving formation and the second receiving formation, and the electrical conductors are unattached to the shape-imparting element carrier such that the electrical conductors may remain in the electrode sheath in situ when the shape-imparting element carrier is removed from the holder.

12. The modular catheter assembly of claim 1, wherein an axially-extending bore of the holder is a blind bore defined at the distal end of the holder.

13. The modular catheter assembly of claim 12, wherein the shape-imparting element further comprises an actuator received in the elongate tubular member.

14. The modular catheter assembly of claim 13, wherein the shape-imparting element carrier is removably received within the blind bore, one of the elongate tubular member and the actuator of the shape-imparting element being fast with the shape-imparting element carrier and the other of the elongate tubular member and the shape-imparting element being fast with the holder.

15. The modular catheter assembly of claim 14, wherein the shape-imparting element carrier functions as a control mechanism for controlling the shape of the shape-imparting element carried on the shape-imparting element carrier, the control mechanism being axially displaceable relative to the holder.

16. The modular catheter assembly of claim 15, wherein the electrode sheath carrier is arranged distally of the shape-imparting element carrier, the electrode sheath carrier having a proximally-extending mount received in a distal part of the holder.

17. The modular catheter assembly of claim 16, wherein the electrode sheath carrier includes a displacement mechanism displaceably arranged, axially, on the mount for effecting axial displacement of the electrode sheath relative to the shape-imparting element, in use.

18. The modular catheter assembly of claim 14, further including a first sealing element interposed between the shape-imparting element carrier and the distal end of the holder for inhibiting an ingress of material into the axially-extending bore of the holder.

19. The modular catheter assembly of claim 18, further including a second sealing element arranged in the electrode sheath carrier between the mount and the displacement mechanism for inhibiting an ingress of material into an interior of the electrode sheath carrier.

20. A modular catheter assembly, including:
a handle including a first receiving formation and a second receiving formation, the first receiving formation and the second receiving formation comprising a locking mechanism;
a shape-imparting element attached to the handle, the shape-imparting element comprising an elongate tubular member with an actuator received within the elongate tubular member, the actuator being fast with the elongate tubular member at a distal region of the elongate tubular member;
a first detachable member to which one of the elongate tubular member and the actuator is connected, the first detachable member including a first engaging formation; and
a second detachable member, displaceably arranged relative to the first detachable member to which the other of the elongate tubular member and the actuator is connected, the second detachable member including a second engaging formation, wherein each of the first receiving formation and the first engaging formation and the second receiving formation and the second engaging formation are jointly rotatable for de-attachment and re-attachment of the handle and the shape-imparting element by operation of the locking mechanism, the locking mechanism operable by joint rotation of the first detachable member and the second detachable member relative to the handle, the first detachable member and the second detachable member configured to be unlocked from the handle by rotation of the first detachable member and the second detachable member relative to the handle, wherein the elongate tubular member is connected to the first detachable member and the second detachable member while the shape-imparting element is de-attached from the handle.

21. The modular catheter assembly of claim 20, wherein the first detachable member is a boss received within a catheter handle holder, and wherein the second detachable member is a connector receivable within the catheter handle holder distally of the boss.

22. The modular catheter assembly of claim 20, wherein the first detachable member is a catheter handle holder, and wherein the second detachable member is a control mechanism displaceably arranged at a distal end of the catheter handle holder.

23. The modular catheter assembly of claim 20, wherein the first engaging formation and the second engaging formation each comprise at least one protrusion that cooperatively locks into place with the respective first receiving formation and the second receiving formation when the shape-imparting element carrier is turned within the handle.

24. The modular catheter assembly of claim 20, wherein at least one of the first receiving formation and the second receiving formation includes an L-shaped slot.

25. The modular catheter assembly of claim 20, wherein at least one of the first receiving formation and the second receiving formation includes a keyway-shaped slot.

* * * * *